US005478749A

United States Patent [19]
Dyke

[11] Patent Number: 5,478,749
[45] Date of Patent: Dec. 26, 1995

[54] METHOD AND ARTICLE FOR PROVIDING AN INDICATION OF THE PRESENCE OF AIR IN STEAM

[76] Inventor: Denis G. Dyke, 11951 Angling Rd., Edinboro, Pa. 16412

[21] Appl. No.: 139,465

[22] Filed: Oct. 20, 1993

Related U.S. Application Data

[63] Continuation of Ser. No. 13,147, Feb. 1, 1993, Pat. No. 5,270,217.

[51] Int. Cl.⁶ .................................................. G01N 31/22
[52] U.S. Cl. .............................. 436/127; 422/26; 422/58; 422/61; 436/138
[58] Field of Search .................................. 422/11, 26, 58, 422/27, 32, 292, 298, 305, 61; 436/127, 138

[56] References Cited

U.S. PATENT DOCUMENTS

| | | | |
|---|---|---|---|
| 2,844,026 | 7/1958 | Wischmeyer et al. | 422/58 |
| 3,479,131 | 11/1969 | Scoffield et al. | 422/119 |
| 3,967,494 | 7/1976 | Joslyn | 422/205 |
| 4,115,068 | 9/1978 | Joslyn | 422/56 |
| 4,594,223 | 6/1986 | Dyke et al. | |

OTHER PUBLICATIONS

"Union Carbide Molecular Sieves", publication F–1979F, Sep. 1983 3M, Lithographed in USA.

*Primary Examiner*—Lyle A. Alexander
*Attorney, Agent, or Firm*—Eugene E. Renz, Jr.

[57] ABSTRACT

A method and apparatus for evaluating the efficacy of prevacuum steam sterilizers by separating, collecting and detecting the presence of air in association with steam. A receptacle containing an adsorbent directly separates air from steam without changing the physical state of the steam. The apparatus has a portal communicating with the sterilizing environment and a defined path for the steam to traverse from the portal to a distal end of the apparatus. The distal end of the apparatus is attached to an air collection chamber which contains an air indicator. The indicator can be chemical or biological, and indicated whether any air pockets existed in the steam.

10 Claims, 3 Drawing Sheets

METHOD AND ARTICLE FOR PROVIDING AN INDICATION OF THE PRESENCE OF AIR IN STEAM

This is a continuation of application Ser. No. 08/013,147 filed on Feb. 1, 1993 now U.S. Pat. No. 5,270,217.

BACKGROUND OF THE INVENTION

1. Field of the Invention

The present invention relates to devices for evaluating the efficacy of steam sterilizers, and, more specifically, to devices that provide an indication of the presence of air in a sterilizer during the sterilization process.

2. Description of the Prior Art

Steam sterilization of an object is accomplished by placing steam in contact with the object. The object is cooler than the steam. Thus, the latent heat of the steam is transferred to the object. The latent heat of steam, which is 540 calories per gram makes steam particularly attractive as a sterilizing medium. For example, use of dry air at 320° F. requires exposure for 60 minutes to achieve sterilization equivalent to that obtained by exposure for approximately 15 minutes to saturated steam at 250° F.

To achieve effective steam sterilization, the steam should be fully saturated, that is, without the presence of contaminants such as air. If air is present within the steam, repeated collapse of the steam against the cooler surface of the object to be sterilized will occur, causing accumulation of air and the formation of an air pocket. Air pockets shield microorganisms on the object from the steam, and prevents transfer of a sufficient quantity of heat to the object, resulting in ineffective sterilization. Accordingly, prevacuum steam sterilizers remove air from the sterilization chamber prior to the introduction of pressurized vapor, or steam, into the chamber during the sterilization cycle. However, an ineffective prevacuum cycle can leave air in the chamber, which will remain there and accumulate during the sterilization cycle. Also, air can be introduced into the chamber as a result of equipment leaks and malfunctions, and through the steam supply.

To detect the presence of air during steam sterilization processes, Dr. J. Bowie and Mr. J. Dick described in 1963 a test pack that monitors prevacuum sterilization. The test pack consisted of 29 huckaback towels folded into fourths along their lengths and doubled across their widths to give eight thicknesses of cloth. Each folded towel was stacked, and steam sensitive autoclave tape, formed to resemble a St. Andrew's cross, was placed at various levels in the pack. The pack was placed within a dressing casket or overwrapped in fabric, and placed in the sterilization chamber. After the evacuation cycle had been conducted, steam was introduced into the chamber, where it entered the test pack and collapsed to water as it transferred its latent heat to the cooler towels. Any air that was present in the steam accumulated as the steam collapsed. The air was forced by the pressure within the sterilizer toward the density center of the test pack, where it formed pockets. Any air remaining in the test pack after the evacuation cycle also would be forced by the steam to the density center of the pack. The autoclave tape, through its steam indicator ink, detected the resulting air pockets. A uniform change in color of the steam sensitive indicator ink on the tape, from white to black, indicated completion of a successful sterilization cycle. However, an incomplete color change of the ink indicated an ineffective sterilization cycle. Accordingly, any air that migrated to the indicator ink located at the density centers of the test pack prevented steam from making contact with the entire indicator and, thus, prevented the ink from undergoing a uniform color change. The Bowie-Dick test is discussed further in *The Lancet*, Mar. 16, 1963, pp. 586–587. The Bowie-Dick protocol is further described in the National Standards and Recommended Practices for Sterilization: Recommended Practice—Good Hospital Practice—Steam Sterilization and Sterility Assurance, ¶6.7 (1988), published by the Association for the Advancement of Medical Instrumentation, 3330 Washington Boulevard, Arlington, Va. 22201.

The Bowie and Dick test pack performed several functions. First, and most basically, it separated steam from any air present in the steam, since the towels functioned like a heat sink, and included an indicator that indicated contact with steam. Importantly, it provided a "challenge" to the removal of air during the evacuation cycle. That is, it was more difficult to remove air from the test pack than it was to remove air from the objects that were to be sterilized, due to the natural entrapment of air by the interstices of the towels forming the test pack. Thus, the absence of air pockets from the test pack during sterilization justified the conclusion that air pockets were not present anywhere in the chamber during the sterilization process. Similarly, the test pack provided a "challenge" to the entry of steam into the test pack during the sterilization cycle, justifying the conclusion that steam had adequately contacted the articles undergoing sterilization if the indicator ink on the tape in the pack changed color uniformly. Finally, the towels of the test pack adsorbed the water created by the collapsing steam, thus preventing it from travelling to the autoclave tape where it could revaporize and contribute to a false indication. In summary, then, the Bowie and Dick test pack offered (i) a challenge to removal of air from the test pack, (ii) a heat sink that absorbed the latent heat of steam and separated air and steam, (iii) resistance to penetration by steam into the pack, (iv) an indicator that detected, the presence of air and (v) an absorbent that retained the water generated by the change of state of the steam.

Nonetheless, Bowie and Dick type testing proved less than satisfactory due to the need for cotton towels, varying directions by manufacturers in the use of their indicator sheets, variations in folding techniques, non-uniform towel conditions, variations in the outer wrapping material utilized, and the presence of laundry chemicals on the towel, which could react with the indicator. Therefore, workers in the art attempted to develop devices for indicating the presence of air during sterilization that afforded more uniformity in use, and more reliable results, and that provided the benefits of the Bowie-Dick test pack.

Joslyn U.S. Pat. No. 4,115,068 discloses an air indicating device for use in a steam or gas sterilizer comprising an upright, insulated tube with a closed top and open bottom. The upper portion of the tube contains a thermal indicator surrounded by a heat sink material. Steam enters the tube through the bottom and is forced toward the top of the tube. The steam that contacts the heat sink will be condensed; however, the steam that contacts the indicator strip will transfer its heat and humidity to the strip. As the temperature of the heat sink rises during the sterilization cycle, it can revaporize the condensed steam, which will provide a false indication of the presence of saturated steam. Additionally, the tube does not offer a challenge to air removal during the evacuation cycle, and it does not offer resistance to steam penetration during the sterilization cycle.

Augurt U.S. Pat. No. 4,486,387 discloses a disposable test pack for determining the effectiveness of a prevacuum steam sterilization cycle. The pack consists of a steam indicator sheet placed between stacks of porous paper sheets. The pack is intended to simulate a Bowie-Dick test pack. However, the evacuation of air from and introduction of steam into the stack will occur on all six sides of the test pack, and will tend to follow the path of least resistance. Further, the stack of porous sheets consists of an inner "core" of sheets and an outer "shell" of sheets. The sheets constituting the "core" are of a porosity that is lower than those constituting the "shell." Therefore, air and steam travel will occur to a greater extent through the inner "core," and the desired effect of the two different porosities is eliminated. Also, depending on the smoothness and degree of contact among the sheets, within each layer, the flow of steam into the stack will vary, and, correspondingly, the indicator will give varying results. Finally, the degree of dryness of the paper forming the layers will affect the indication provided by the stack.

Dyke and Oshlag U.S. Pat. No. 4,594,223 discloses an insulated heat sink placed in "series" with a chamber containing an indicator for detecting the presence of-air within a steam sterilizer. The heat sink can be fibrous or a metal coated with an insulator. As steam contacts the heat sink it gives up its latent heat, which cause the steam to change state, and accumulate any air mixed with the steam. Newer prevacuum steam sterilizers use a conditioning-evacuation cycle prior to sterilization, which replaces the original deep or continuous evacuation. This newer cycle typically commences with a one minute steam purge with the drain open followed by a vacuum pulse and three intermittent steam and vacuum pulses with the drain closed. Each pulse occurs at a prescribed pressure to condition the load and eliminate air prior to sterilization. During the steam purge and pulses, the temperature of the heat sink rises, and its ability to function is compromised. Therefore, the heat sink cannot effectively separate air from steam during the critical sterilization cycle.

Accordingly, despite the efforts of workers in the art, there remains a need for an effective indicator of the presence of air during steam sterilization that provides the benefits of a Bowie-Dick test pack.

SUMMARY OF THE INVENTION

All current Bowie and Dick type devices use a heat sink, which must change the state of steam to water to accumulate any air in the steam. The capacity of the heat sink is limited, and, thus, often is rendered ineffective during the sterilization cycle to collapse steam. The present invention accumulates any gas in the steam without the need for a heat sink: The present invention employs a material that colectively absorbs water That is, the material adsorbs the steam but does not adsorb air present within the steam. The physical structure of the material, and not its ability to absorb heat, permits it to separate air from steam. The capacity of the material permits it to remain effective well into the sterilization cycle. Also, some water can be desorbed from the material by exposing it to a vacuum Thus, the capacity of the material is regenerated to some extent during pre-sterilization evacuation cycles.

Therefore, the present invention can function to separate air from steam further into the sterilization cycle than other indicators. The present invention also retains the remaining benefits provided by a Bowie-Dick test pack.

BRIEF DESCRIPTION OF THE DRAWINGS

The following detailed description of the preferred embodiments can be understood better if reference is made to the attached drawing, in which.

DETAILED DESCRIPTION OF THE PREFERRED EMBODIMENTS

Figure 1:
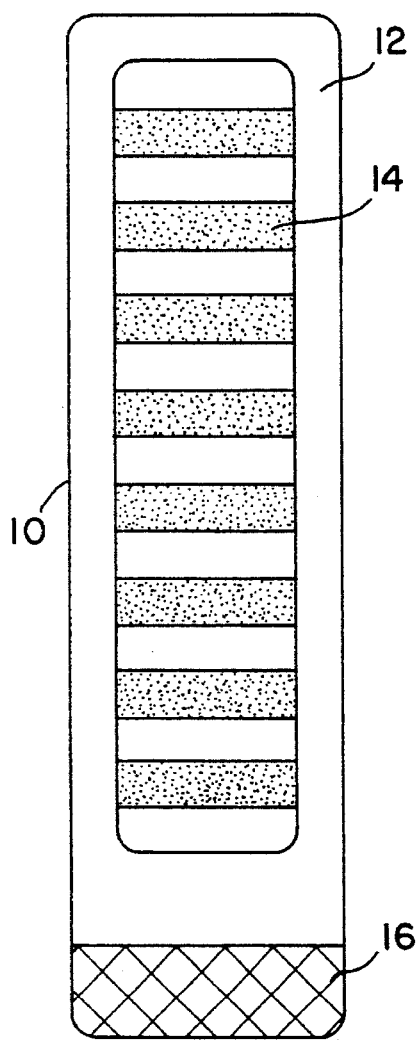
FIG. 1 is a top plan view of the preferred indicator provided by the present invention.

By way of introduction, newer prevacuum steam sterilizers use an evacuation cycle that is actually a combination of conditioning and evacuation. This combination compromises the use of a heat sink in its ability to separate air from steam. During this cycle, typically a one minute steam purge is initially conducted with the drain open. Then a vacuum pulse and three additional steam and prevacuum pulses are conducted in a closed system. Each pulse reaches a critical pressure. The heat transferred from the initial steam purge and subsequent pulses reduces the heat absorptive capabilities of a heat sink. Therefore, the present invention employs a material that does not rely on a temperature difference between the steam and a part of the indicator, usually a heat sink, to collapse steam to separate air from it. The present invention employs a material that physically adsorbs steam but not air, due to its structure. Thus, any heating of the material during any part of the cycle does not compromise its ability to function. In fact, due to the structure of the material, the material has a capacity sufficient to separate air from steam during pre-sterilization cycles and the sterilization cycle itself. Any regenerative capabilities of the material simply enhance its capacity. The material can be an adsorbent a desiccant, or any other suitable material.

For example, the metal alumino-silicate crystals that are employed by the preferred embodiments of the present invention instead of a heat sink physically adsorb steam during each conditioning steam pulse. That steam is desorbed to some extent during each vacuum pulse, thereby regenerating the adsorbent somewhat before the sterilization cycle is commenced. This desorption actually is aided by the temperature increase of the adsorbent during the process. Thus, unlike a heat sink, this class of materials can detect all steam-air problems since its utility can extend well into the sterilization portion of the cycle.

In the construction of devices 10, 100 and 200, which are shown in FIGS. 1 through 6, steam is constrained to follow a prescribed path. Steam enters the device through a sealable opening into a receptacle containing an adsorbent. The receptacle is designed to provide maximum contact between the steam and the adsorbent, and it can define a torturous path to further this purpose. At the distal end of the receptacle is a small opening that provides communication between the receptacle and an air collecting chamber. The chamber contains an indicator. The indicator can be a typical known biological or chemical indicator, or it can be a combination indicator of known type. As is well known in the art, a chemical indicator includes a steam sensitive ink, which changes color upon exposure to steam. As is also well known in the art, a biological indicator includes microorganisms that will be destroyed during steam sterilization. A variety of chemical and biological indicators are commercially available.

The top section of the device, which seals the air collecting chamber and covers the indicator, can be peeled or broken away to retrieve the indicator for record purposes.

In use, a tab covering the entrance opening to the adsorbent receptacle is removed and the device is, typically, placed in the coolest section of the sterilizer, usually over the drain, where air is likely to be present. During the evacuation portion of the cycle, air is withdrawn from the interstices of the adsorbent receptacle and air collecting chamber. Entering the sterilization portion of the cycle, steam is forced into the adsorbent receptacle where it is selectively adsorbed by the adsorbent material. Any air mixed with the steam is not adsorbed and is forced further through the receptacle in a progressive manner as areas of the adsorbent becomes saturated. When the adsorbent is totally saturated, the air and steam forced into the air collecting chamber. Here, if air is present, it will be forced to the end distal from the opening to the receptacle, and it will shield the indicator, thus preventing a uniform change that would show complete reaction with steam. Upon completion of the sterilization cycle, the device is withdrawn from the sterilizer and a determination of the effectiveness of the cycle can be made.

FIGS. 1 through 6 show the preferred embodiments of the indicator provided by the present invention. FIGS. 1 through 4 show an indicator 10, which is typically placed within the chamber of a prevacuum type steam sterilizer (not shown) for the purpose of detecting and indicating inadequate air removal during evacuation, and introduction of air during evacuation through a leak or during the sterilization cycle.

Figure 2:
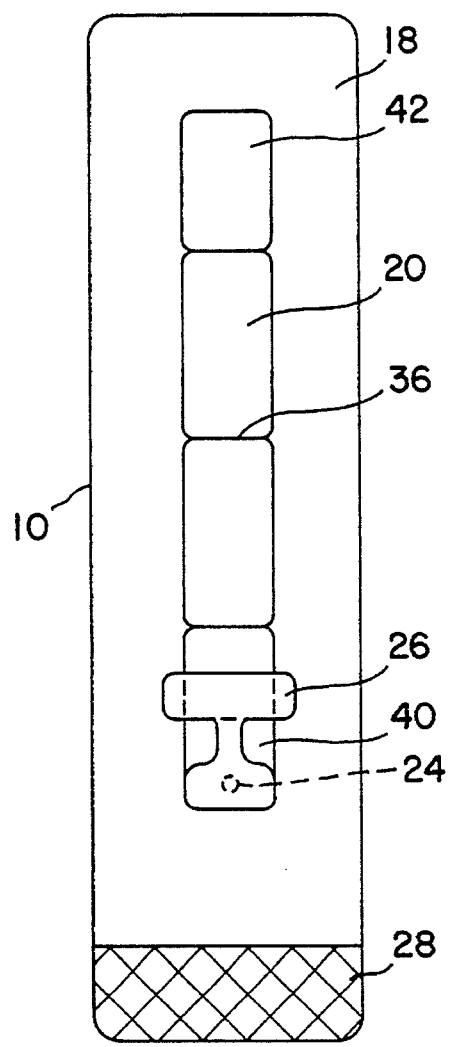
FIG. 2 is a bottom view of the indicator shown in FIG.

Device 10 includes a top 12, and a housing 18, which includes a section 30 that is sealed along its perimeter to housing 18. The assembly of housing 18 and section 30 is sealed along the perimeter of housing 18 to top 12. Device 10 includes an indicator strip 14 located beneath top 12, and a grip section 16, which forms a part of top 12. Referring to FIG. 2, housing 18 defines adsorbent receptacle 20 that is adapted to contain a steam adsorbent 22. Housing 18 also defines a portal 24 which allows steam to enter housing 18. A tab 26 is secured to the bottom of housing 18 over portal 24. Tab 26 maintains the integrity of the interior of housing 18 and adsorbent 22 during shipping and storage of device 10. Section 28, which is defined by housing 18 cooperates with section 16 of top 12 to provide a grip for device 10. Top 12, including section 16, is so secured to housing 18 as to permit a user to peel top 12 from housing 18 to gain access to indicator 14. Indicator 14 is, for discussion purposes, a chemical indicator. That is, indicator 14 includes steam sensitive ink.

Figure 3:
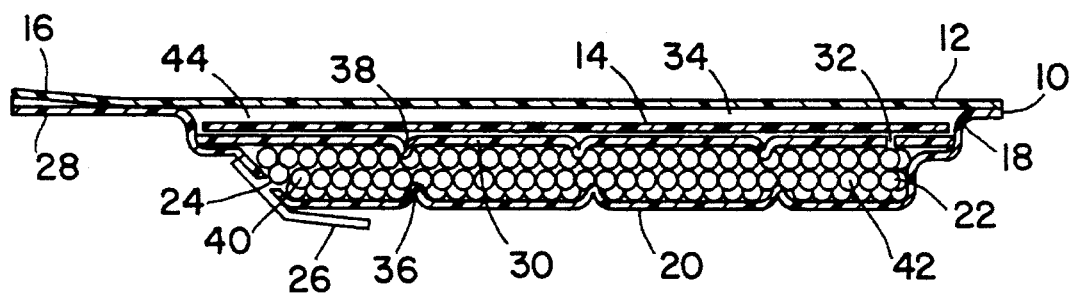
FIG. 3 is a side sectional view of the indicator shown in FIG. 1.
Figure 4:
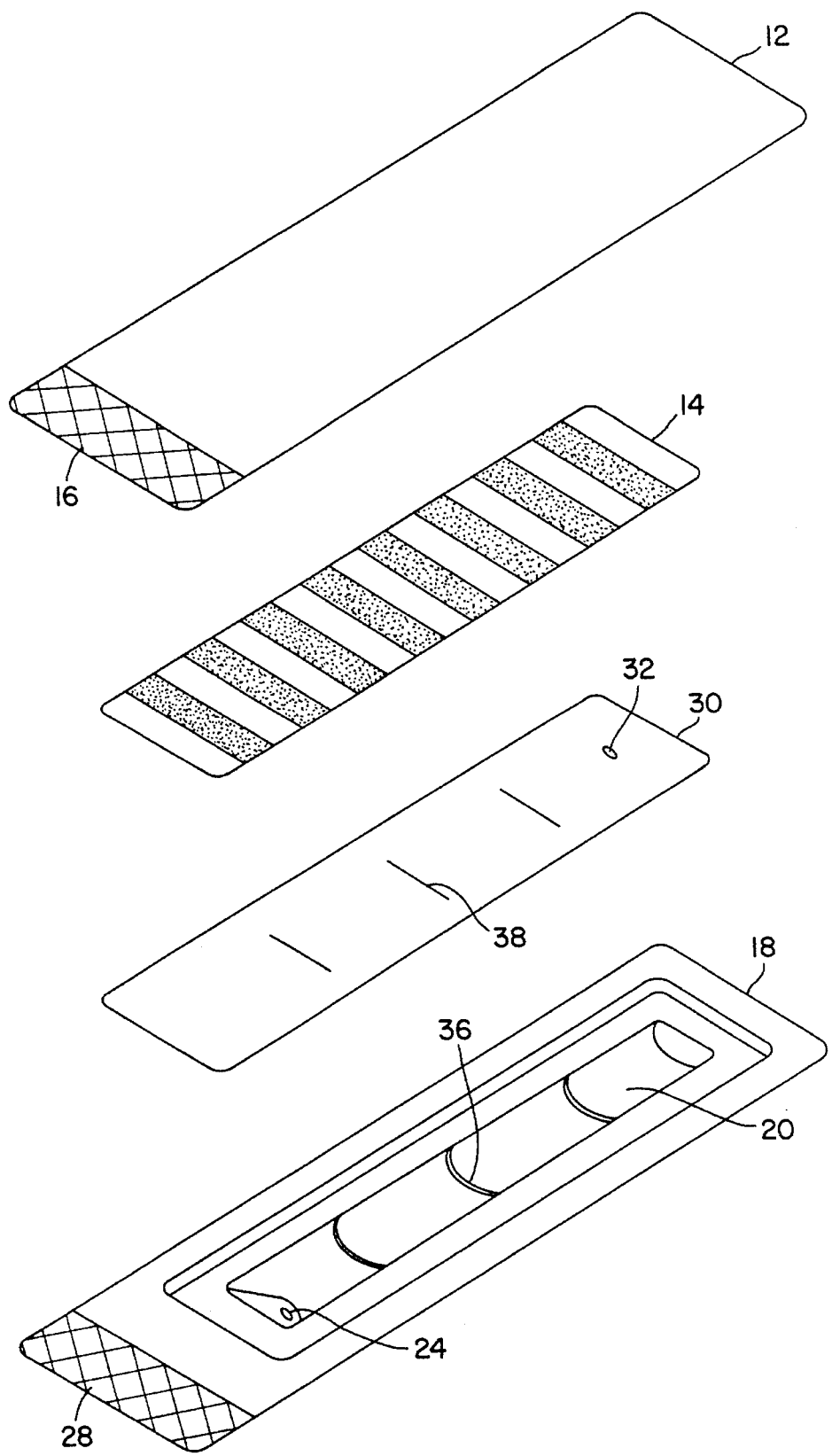
FIG. 4 is an isometric, exploded view of a portion of the indicator shown in FIG. 1.

Referring to FIG. 3, section 30 is sealed to housing 18 to enclose receptacle 20. Section 30 also cooperates with top 12 to define an air collection chamber 34, in which indicator 14 is located. Adsorbent 22 can be loaded into receptacle 20 prior to securing section 30 in place. Alternately, adsorbent 22 can be loaded into receptacle 20 through portal 24 after section 30 has been secured to housing 18. Air collection chamber 34 is in communication with receptacle 20 through a portal 32, which is defined by section 30. Preferably, the components shown in FIG. 4 are assembled together by securing section 30 to housing 18, placing indicator strip 14 on top of section 30, and securing top 12 to housing 18.

The preferred adsorbent 22 for device 10 is crystalline metal alumino-silicates and, more specifically, $Na_{86}[(AlO_2)_{86}(SiO_2)_{106}] \times H_2O$, which has been activated for water adsorption by removing the water of hydration by heating. Crystalline metal alumino silicates of the type preferred can be purchased from Union Carbide Corporation, Danbury, Conn. The crystal structure of the metal alumino-silicates is a truncated octahedra joined in a cubic array, or honeycomb structure, with relatively large cavities. Each cavity is connected with six adjacent cavities through apertures. The efficiency of this material for this application is the selective adsorption of water resulting from water's unique molecular size and polarity, along with the uniform size and molecular dimensions of the crystal's cavities, the extremely large surface area resulting from the honeycomb, and the high capacity for adsorption over a wide range of operating conditions including temperatures to over 600° F. Additionally, the large volume of air within an aggregate of crystals offers a challenge to air removal during the evacuation portion of the steam sterilization cycle. The quantity of adsorbent will vary with the application in a manner understood by those of ordinary skill in the art upon reference to manufacturers' published information. The sizing of housing 18 will depend on the quantity of material it must contain.

To use device 10, tab 26 is removed from the bottom of housing 18, and device 10 is placed in the chamber of a prevacuum steam sterilizer. During the newer pulsing prevacuum cycle, the initial steam purge forces some steam through portal 24 and into receptacle 20, where it is adsorbed by adsorbent 22 located at proximal end 40 of receptacle 20. Following the initial steam purge, and each subsequent steam pulse cycle, during which steam is adsorbed by adsorbent 22, an evacuation pulse is produced. During each evacuation pulse, adsorbed moisture is desorbed to some extent and exits receptacle 20 through portal 24. Thus, adsorbent 22 is regenerated to some extent during each evacuation pulse. The initial steam purge and each subsequent steam pulse occurring during the conditioning-evacuation portion of the cycle increase the temperature of device 10, including absorbent 22. During the evacuation pulses, air exits adsorbent 22, through portal 24, and air collecting chamber 34, through portal 32. As steam enters the sterilizer chamber, it is forced into device 10 through portal 24. Upon contacting adsorbent 22, the steam is adsorbed, leaving any air present in the steam, even if the adsorbent 22 is at the sterilization temperature. Thus, unlike devices that rely on heat sinks to separate air from steam, the efficacy of device 10 extends throughout the sterilization cycle. As the steam front progresses from proximal end 40 of receptacle 20 to distal end 42, it forces any accumulated air ahead of it through receptacle 20. Baffles 36 and 38 formed in sections 18 and 30, respectively, define a tortuous path for steam traveling through receptacle 20, and create turbulence in the steam. Turbulence in the steam flow aids intimate contact between the steam and adsorbent 22. Ultimately, the steam forces any accumulated air through portal 32 and into air collecting housing 34. If air is not present in chamber 34, which means the sterilization cycle was successful, the ink on chemical indicator will have changed color uniformly. Otherwise, the color change will not be uniform.

Figure 5:
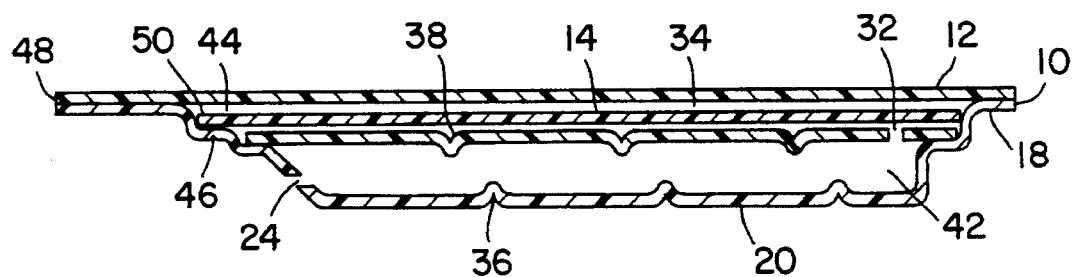
FIG. 5 is a side, sectional view of an alternate indicator provided by the present invention.
Figure 6:
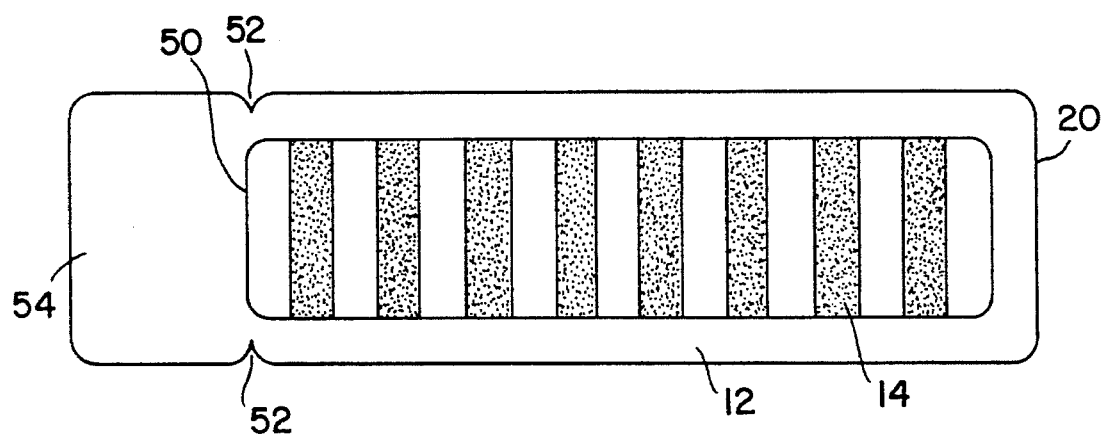
FIG. 6 is a top plan view of another alternate indicator provided by the present invention.

FIGS. 5 and 6 show devices 100 and 200, which include alternative arrangements for providing access to air collecting chamber 34 and indicator strip 14. Elements shown in FIGS. 5 and 6 have been assigned the reference characters of the corresponding elements shown in FIGS. 1 through 4. The housing 18 of each of devices 100 and 200 is made from a suitable plastic material. As is well-known to those in the art, a plastic material will exhibit lower tear and crack resistance to forces applied along the molecular orientation of the plastic than to forces applied perpendicular to the molecular orientation. The molecular orientation of housing 18 of each of devices 100 and 200 should be 90° to the longitidinal axis of housing 18. The molecular orientation of top 12 of device 200 should also be 90° to the longitidinal axis of device 10.

A detente 46 is formed in the bottom surface of housing 18 of device 100 across its width. Access to end 50 of strip 14 is gained by bending end 48 of top 12 and tab 28 of housing 18 upward, relative to the orientation of device 100 in FIG. 5, thereby applying a focused stress along detente 46, until a fracture occurs.

Top 12 of device 200 defines a pair of detentes 52. Detentes 52 facilitate tearing end 16 away from housing 18 and the remainder of top 12 to gain access to end 50 of strip 14.

The preferred method provided by the present invention employs devices 10, 100, or 200 during sterilization to indicate the effectiveness of the sterilization cycle.

What is claimed is:

1. A method for the detection of air in a closed sterilization system comprising the steps of:
   a. placing an air indicating device into a sterilization chamber;
   b. creating an atmosphere capable of sterilization in the chamber by alternating introduction of vacuum and steam to substantially remove air within said chamber and fill said chamber with steam at sterilization conditions;
   c. said steam at sterilization conditions contacting the air indicating device, the device which comprises a column containing an absorbent that directly removes the steam by a process selected from the group consisting of absorption, adsorption and combinations thereof, without a change of state of the steam to a liquid liberating any air inadvertently mixed with the steam and an indicator for detecting the presence of the liberated air;
   d. observing the indicating device to determine whether there was air present within the steam in the chamber.

2. The method of claim 1 wherein said test device includes a housing defining a column and a quantity of absorbent contained therein, said housing defining a column in which steam is introduced into the proximal end of the column and is forced to travel progressively to the distal end of said column.

3. The method of claim 2 wherein said column further includes an adjacent chamber proximate its distal end for collection of air, said chamber further including means for indicating the presence of air concentrated in said chamber.

4. The method of claim 3 wherein said absorbent is a metal alumino-silicate.

5. The method of claim 4 wherein said metal alumino-silicate is $Na_{86}[(AlO_2)_{86}(SiO_2)_{106}] \cdot XH_2O$, with a portion of the water of hydration being removed prior to use.

6. A device for the detection of air in a closed sterilization system comprising:
   a. an air indicating device placed into a sterilization chamber;
   b. means for creating an atmosphere capable of sterilization in said chamber by alternating introduction of vacuum and steam pulses to substantially remove air within said chamber and fill said chamber with steam at sterilization conditions;
   c. means for passing said steam at sterilization conditions in contact with the air indicating device, the device which comprise a column containing an absorbent that directly removes the steam by a process selected from the group consisting of absorption, adsorption and combinations thereof, without a change of state of tire steam to a liquid liberating any air inadvertently mixed with the steam and an indicator for detecting the presence of the liberated air.

7. The device of claim 6 wherein said test device includes a housing defining a column and a quantity of absorbent contained therein said housing defining a column in which steam is introduced into the proximal end of tire column and is forced to travel progressively to the distal end of said column.

8. The device of claim 5 wherein said column further includes an adjacent chamber proximate its distal end for collection of air said chamber further including means for indicating the presence of air concentrated in said chamber.

9. The device of claim 8 wherein said absorbent is a metal alumino-silicate.

10. The device of claim 9 wherein said metal alumino-silicate is $Na_{86}[(AlO_2)_{86}(SiO_2)_{106}] \cdot XH_2O$, with a portion of the water of hydration being removed prior to use.

* * * * *